United States Patent [19]

Garcia

[11] Patent Number: 4,599,748
[45] Date of Patent: Jul. 15, 1986

[54] PROTECTIVE KNEE GUARD

[75] Inventor: Ruben C. Garcia, Corpus Christi, Tex.

[73] Assignee: Francis R. Shearer, Corpus Christi, Tex. ; a part interest

[21] Appl. No.: 714,810

[22] Filed: Mar. 22, 1985

[51] Int. Cl.⁴ .............. A41D 13/00; A41D 13/06; A61F 3/00
[52] U.S. Cl. ............................. 2/22; 128/80 C; 2/24
[58] Field of Search .............. 2/22, 24, 62; 128/80 R, 128/80 C, 80 F, 80 E, 88

[56] References Cited

U.S. PATENT DOCUMENTS

| 3,898,697 | 8/1975 | Whitehead | 128/80 C |
| 4,068,312 | 1/1978 | Ledesma | 128/80 |
| 4,136,404 | 1/1979 | Lange | 2/22 |
| 4,139,002 | 2/1979 | Almedia | 2/22 |
| 4,271,831 | 6/1981 | Deibert | 2/22 |
| 4,372,298 | 2/1983 | Lerman | 128/80 C |
| 4,387,709 | 6/1983 | Shen . | |
| 4,388,920 | 6/1983 | Hajost et al. | 128/88 |
| 4,409,689 | 10/1983 | Buring et al. | 2/22 |
| 4,502,472 | 3/1985 | Pansiera | 128/80 F |

Primary Examiner—Ronald Feldbaum
Attorney, Agent, or Firm—G. Turner Moller

[57] ABSTRACT

A protective knee guard is provided to shield the wearer's knee from injuries due to impact on the knee, from twisting of the knee and the like. The knee guard comprises a pair of rigid arcuately shaped guards. One of the guards is attached to a pivoted brace frame at a location above the knee so that the arcuate guard portion extends downwardly over the knee. The second guard portion is attached to the frame below the knee and extends upwardly so that the arcuately guard portion overlies the knee. In a straight leg position of the wearer, the arcuate guard portions are nested one under the other. As the wearer bends the knee, the guard portions unnest until they reach a position where the ends overlap only slightly, if at all.

14 Claims, 5 Drawing Figures

PROTECTIVE KNEE GUARD

This invention relates to a protective knee guard which may be used by any individual concerned over injury to a knee. Typical users include athletes with knee injuries, persons recuperating from extensive knee surgery and the like.

The prior art includes a wide variety of disclosures for protective knee guards. At present none of these devices are commercially available thereby indicating a judgement in the market place that they have one or more serious disadvantages. Typically, the devices are too expensive, are insufficiently flexible to allow vigorous movement or do not provide substantial protection to the knee against injury from impact or against injury from twisting. Typical prior art protective devices are found in U.S. Pat. Nos. 4,068,312; 4,387,709 and 4,409,689.

This invention is directed at the provision of a protective knee guard which is attached to the wearer's leg much like a conventional knee brace. Attached to that portion of the guard above the knee is a rigid shell having an arcuate guard portion which depends over the knee. A second rigid shell is attached to the guard at a location below the knee and extends upwardly to nest with the first arcuate guard portion.

When the wearer is standing or has the protected leg in a generally straight position, the guard portions nest, one under the other. As the user bends the knee, as during walking or running, the guard portions pivot relative to each other and unnest. Preferably, the leading edges of the guard portions overlap in all positions of the guard so that any impact on the knee is directed onto the guard portions and transferred through them to the leg of the wearer above and below the knee.

In summary, this invention comprises a protective knee guard including a first rigid member providing a first arcuate guard portion overlying the knee of a wearer, a second rigid member providing a second arcuate guard portion overlying the same knee of the wearer, means for releasably attaching the first member to the leg of the wearer at a location above the knee, means for releasably attaching the second member to the leg of the wearer at a location below the knee and means mounting the first and second members for relative pivotal movement between a first generally aligned position corresponding to a straight leg position of the wearer wherein the first and second arcuate guard portions are substantially nested over the knee and a second position wherein members are inclined to each other corresponding to a bent leg position of the wearer wherein the first and second arcuate guard portions are substantially unnested.

It is accordingly an object of this invention to provide a protective knee guard which provides significant protection to the knee of the wearer against injury from contact to the knee.

Another object of this invention is to provide a protective knee guard which allows vigorous bending movement of the knee, as may occur when running or engaging in contact sports.

Other objects and advantages of this invention will become more fully apparent as this description proceeds, reference being made to the accompanying drawings and appended claims.

Figure 1:
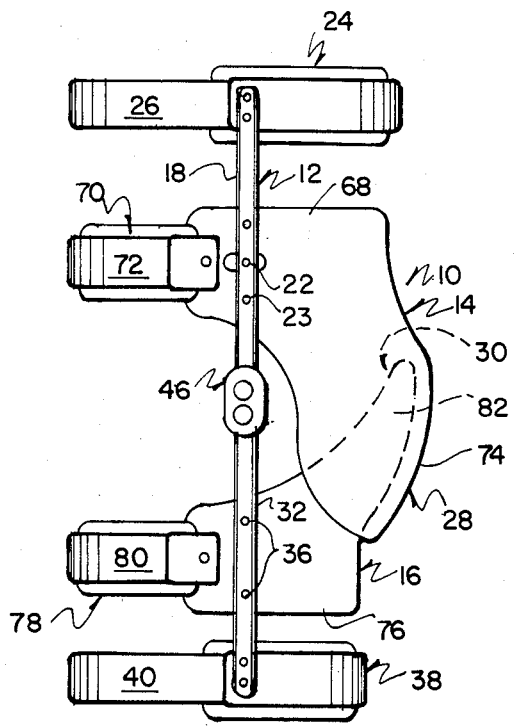
FIG. 1 is side elevational view of the protective knee guard of this invention, illustrated in a straight position of the wearer's leg.
Figure 3:
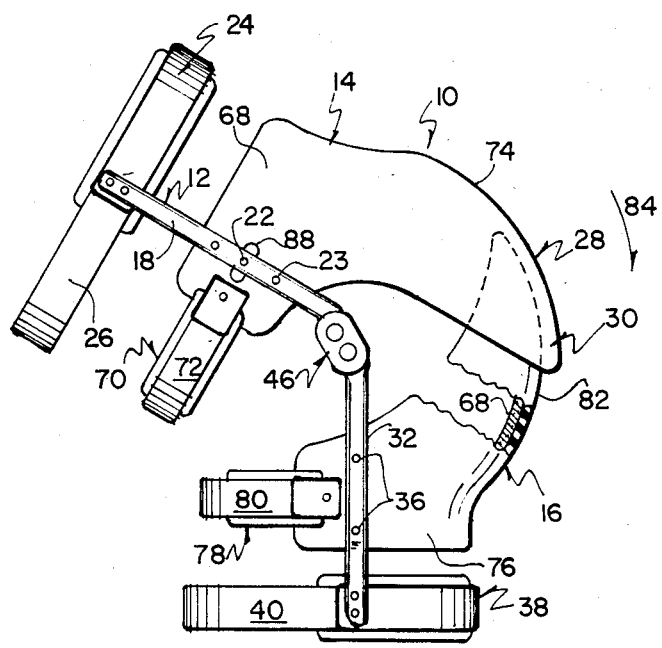
FIG. 3 is a side elevational view, similar to FIG. 1, of a slightly different embodiment of this invention illustrating the guard in the bent position.
Figure 2:
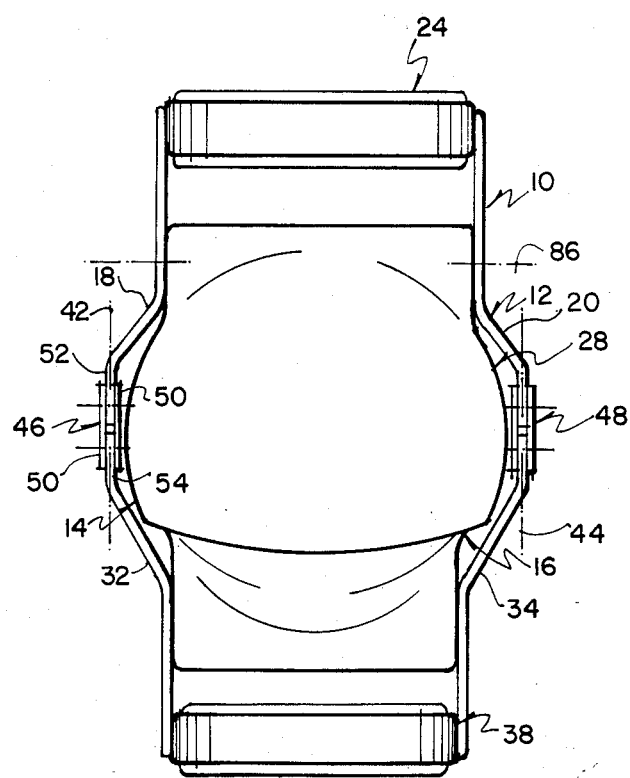
FIG. 2 is a front elevational view of the guard of FIG. 1 illustrated in a straight leg position of the wearer's leg.

Referring to FIGS. 1–3, the protective knee guard 10 of this invention comprises a frame 12 supporting a pair of rigid shells 14, 16 for movement between a first straight leg position shown in FIG. 3 toward a second bent leg position shown in FIG. 1. As will be more fully apparent as this description proceeds, the rigid shells 14, 16 provide a rigid physical barrier against injury to the knee from physical contact from the front or side.

The frame 12 may be of any suitable type and is illustrated as comprising a first pair of elongate metallic members or struts 18, 20 which are connected, in any suitable fashion, to the shell 14 intermediate the ends of the strut 18, as by the use of rivets 22, 23 or the like. The upper ends of the struts 18, 20 carry a padded arcuate side band 24 which extends over the top of the thigh of the wearer. A belt 26 which may be equipped with a buckle, Velcro attachments or the like, is used to temporarily secure the band 24 to the user's leg above the knee.

As shown best in FIG. 2, the struts 18, 20 provide outwardly diverging lower ends receiving therebetween the arcuate guard portions 28, 30 of the shells 14, 16 respectively.

The frame 12 also includes a second pair of rigid metallic members or struts 32, 34. The struts 32, 34 are connected to the rigid shell 16 in any suitable fashion, as by the provision of rivets 36 or the like. Carried on the lower ends of the struts 32. 34 is a padded arcuate shin band 38 having a belt 40 thereon provided with a buckle, Velcro fastener or the like for temporarily securing the shin band 38 below the knee of the wearer.

As shown in FIG. 2, the upper ends of the struts 32, 34 diverge outwardly and terminate in planes 42, 44 in which reside pivotal connections 46, 48 which are preferably identical.

Figure 4:
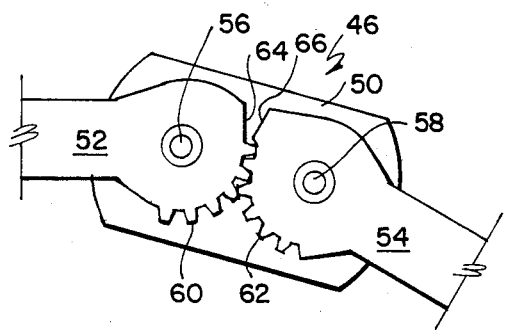
FIG. 4 is a detailed view of the pivotal interconnection between the upper and lower parts of the guard.

As shown best by comparison of FIGS. 2 and 4, the pivotal connection 46 includes a pair of links or plates 50 which receive therebetween the coplanar ends 52, 54 of the struts 18, 32. The strut ends 52, 54 are pivoted to the links 50 by suitable pins 56, 58. The terminal portions of the strut ends 52, 54 are enlarged to provide a series of meshing gear teeth 60, 62. As is evident, the meshing gear teeth 60, 62 extend for an arc of about 90 degrees thereby limiting movement of the struts 18, 32 from the aligned position shown in FIG. 3 to an inclined or bent leg position wherein the wearer's lower leg is disposed about 90° to the upper leg. To this end, the strut ends 52, 54 provide abutting shoulder surfaces 64, 66 which prevent over rotation of the struts 18, 32 beyond the aligned position shown in FIG. 1.

The rigid shells 14, 16 may be made of any suitable material. Although it is possible to make the shells 14, 16 of metal, it is preferred that they be made of a hard tough durable organic polymeric material, such as Kidex. Accordingly, the shells 14, 16 may be conveniently shaped by warming the material until it softens and then fitting the warmed sheet to a cast of the wearer's leg. As shown best in FIG. 1, the shells 14, 16 provide a thin layer of padding 68 which extends substantially throughout the inside of the shells 14, 16. The padding 68 prevents contact of the shells 14, 16 with the wearer's leg.

The shell 14 includes a generally hemicylindrically shaped upper section 68 for receiving the thigh of the wearer. A thigh band 70 is secured to the section 68 and is provided with a belt 72 having thereon a buckle, Velcro fastener or the like for temporarily securing the thigh band 70 above the knee of the wearer. The shell 14 also includes a partial spherically shaped section 74 which merges in any convenient fashion with the section 68.

The shell 16 includes a generally hemicylindrically shaped lower section 76 for receiving the shin of the wearer. A shin band 78 is secured to the section 76 and is provided with a belt 80 having thereon a buckle, Velcro fastener or the like for temporarily securing the shin band 80 below the knee of the wearer. The shell 16 also includes a partial spherically shaped section 82 which merges with the section 76 in any suitable manner.

Because the sections 74, 82 are generally spherical in shape, with the section 82 being slightly smaller, it is possible that the sections 74, 82 can rotate relative to one another to nest and unnest during repeated pivotal movement of the wearer's knee. To this end, it will be evident that the radius of curvature of the sections 74, 82 coincide, or nearly so, with the pivot axes provided by the pins 56, 58.

It will accordingly be seen that the shells 14, 16 overlap the wearer's knee in substantially all angular positions of the frame 12. Even with the frame substantially bent, as in FIG. 3, it will be seen that the possibility of injury to the knee by impact is substantially prevented. Indeed, the only way that impact injury can occur is from a blow from the side at a location between the pivot connection 46 and the shells 14, 16. It will be evident that a blow from this direction will be absorbed by the guard 10 unless it is directed with a small instrument exactly located in the gap between the guard 12 and the shells 14, 16. It will accordingly be seen that the guard 10 provides substantial protection against impact injury to the knee. Because of the construction of the frame 12, thigh band 70 and shin band 78, it will be evident that the guard 10 provides substantial protection against knee injury due to twisting.

As heretofore described, the rigid shell 14 has been assumed to be rigidly connected to the strut 18 of the frame 12. Indeed, a prototype of this invention, with a rigidly connected upper shell, has functioned admirably. Preferably, however, the shell 14 is mounted for limited pivotal movement in a clockwise direction shown by the arrow 84 in FIG. 3. It is desirable, of course, that the shells 14, 16 overlap as much as possible in the inclined positions of the leg. It has been found that the upper shell 14 can be moved downwardly by naturally occuring body motions when the leg is bent. Specifically, it has been learned that the bulging or expansion of the thigh muscles, which occur during bending of the leg, can cause clockwise rotation of the upper shell 14 toward the lower shell 16.

To these ends, the upper shell 14 is mounted for limited pivotal movement about an axis 86 comprising the center line of the rivet 23. A slot 88 receives the rivet 22 and allows limited pivotal movement of the shell 14 about the axis 86.

Figure 5:
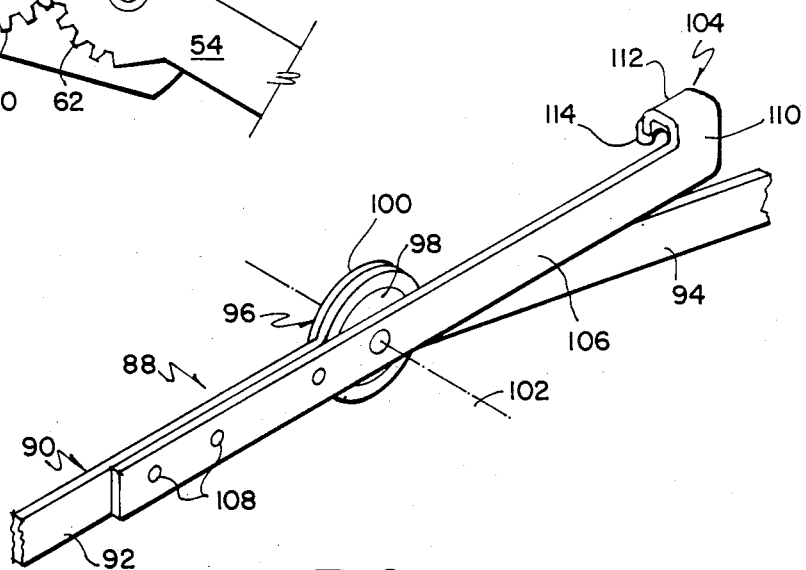
FIG. 5 is an isometric view of another embodiment of a device for limiting pivotal movement of the guard halves.

Referring to FIG. 5, there is illustrated a somewhat different bearing structure. In the embodiment of FIG. 5, the protective knee guard 88 comprises a frame 90 carrying rigid upper and lower shells (not shown). The frame 90 comprises a spaced pair of upper members or struts 92, a similar pair of spaced lower struts 94 which are interconnected by a ball bearing assembly 96. The ball bearing assembly 96 comprises an outer race 98 comprising an enlarged end of the strut 82, an outer race 100 comprising an enlarged end of the strut 94 and a multiplicity of ball bearings (not shown) captivated inside the races 98, 100 providing for low friction pivotal movement about an axis 102. In order to prevent over rotation of the struts 92, 94 tending to bend the knee backwards, a limit mechanism 104 is provided. The limit mechanism 104 comprises a strut 106 secured to the strut 92 by one or more rivets 108. The strut 108 extends from adjacent the strut 92 to a position intermediate the ends of the strut 94. On the free end 110 of the limit mechanism 104 is a curved end 112 adapted to receive the edge of the strut 94. The reverted end 112 is conveniently coated or otherwise provided with a plastic fitting 114.

It will accordingly be seen that there is herein provided an improved protective knee guard having many advantages over the prior art.

While the invention has been described in connection with specific embodiments thereof, it will be understood that it is capable of further modification, and this application is intended to cover any variations, uses or adaptations of the invention following, in general, the principles of this invention and including such departures from the present disclosure has come within known accustomary practice in the art to which the invention pertains and as may be applied to the essential features hereinbefore set forth, and as fall within the scope and spirit of the invention and the limits of the appended claims.

I claim:

1. A protective knee guard comprising
a first rigid member providing a first arcuate guard portion for overlying a knee of a wearer;
a second rigid member providing a second arcuate guard portion for overlying the same knee of the wearer;
means for releasably attaching the first member to the leg of the wearer at a location above the knee;
means for releasably attaching the second member to the leg of the wearer at a location below the knee; and
means mounting the first and second members for relative pivotal movement between a first generally aligned position corresponding to a straight leg position of the wearer wherein the first and second arcuate guard portions are substantially nested over the knee and a second position wherein the members are inclined to each other corresponding to a bent leg position of the wearer wherein the first and second arcuate guard positions are substantially unnested, the mounting means comprises a link between the first and second members and means pivotally mounting the first and second members to the link for relative pivotal movement about a pair of spaced apart pivotal axes.

2. The protective knee guard of claim 1 wherein the mounting means comprises means pivotally mounting the first and second members for relative pivotal movement about a pair of spaced apart pivotal axes.

3. The protective knee guard of claim 2 wherein the mounting means comprises a link between the first and second members, each of the members being pivoted to the link.

4. The protective knee guard of claim 1 wherein the first and second members provide meshing gear teeth between the pivot axes, the gear teeth extending for about a 90° arc for limiting movement of the members between the first and second positions.

5. A protective knee guard comprising
a first rigid member providing a first arcuate guard portion for overlying a knee of a wearer;
a second rigid member providing a second arcuate guard portion for overyling the same knee of the wearer;
means for releasably attaching the first member to the leg of the wearer at a location above the knee;
means for releasably attaching the second member to the leg of the wearer at a location below the knee; and
means mounting the first and second members for relative pivotal movement between a first generally aligned position corresponding to a straight leg position of the wearer wherein the first and second arcuate guard portions are substantially nested over the knee and a second position wherein the members are inclined to each other corresponding to a bent leg position of the wearer wherein the first and second arcuate guard positions are substantially unnested; and
means limiting movement of the first and second members between the first and second positions.

6. A protective knee guard comprising
a first rigid member comprising a rigid organic polymeric shell providing a first arcuate guard portion for overlying a knee of a wearer and a pair of rigid struts;
a second rigid member providing a second arcuate guard portion for overlying the same knee of the wearer;
means carried by the rigid struts for releasably attaching the first member to the leg of the wearer at a location above the knee;
means for releasably attaching the second member to the leg of the wearer at a location below the knee; and
means mounting the first and second members for relative pivotal movement between a first generally aligned position corresponding to a straight leg position of the wearer wherein the first and second arcuate guard portions are substantially nested over the knee and a second position wherein the members are inclined to each other corresponding to a bent leg position of the wearer wherein the first and second arcuate guard positions are substantially unnested.

7. A protective knee guard comprising
a first rigid member providing a first arcuate guard portion for overlying a knee of a wearer;
a second rigid member providing a second arcuate guard portion for overlying the same knee of the wearer;
means for releasably attaching the first member to the leg of the wearer at a location above the knee;
means for releasably attaching the second member to the leg of the wearer at a location below the knee; and
means mounting the first and second members for relative pivotal movement between a first generally aligned position corresponding to a straight leg position of the wearer wherein the first and second arcuate guard portions are substantially nested over the knee and a second position wherein the members are inclined to each other corresponding to a bent leg position of the wearer wherein the first and second arcuate guard portions are substantially unnested; and
means limiting movement of the first and second members beyond the first position during movement of the members from the second position toward the first position.

8. The protective guard of claim 7 wherein the mounting means includes a hook carried by one of the members and a receiver provided by the other member, the engagement of the hook and receiver preventing further relative pivotal movement between the members.

9. A protective knee guard comprising
a first rigid member providing a first arcuate guard portion for overlying a knee of a wearer;
a second rigid member providing a second arcuate guard portion for overlying the same knee of the wearer;
means for releasably attaching the first member to the leg of the wearer at a location above the knee comprising a pair of generally parallel struts and a thigh band attached to the struts for encircling the leg of the wearer above the knee;
means for releasably attaching the second member to the leg of the wearer at a location below the knee; and
means mounting the first and second members for relative pivotal movement between a first generally aligned position corresponding to a straight leg position of the wearer wherein the first and second arcuate guard portions are substantially nested over the knee and a second position wherein the members are inclined to each other corresponding to a bent leg position of the wearer wherein the first and second arcuate guard portions are substantially unnested; and
means mounting the first rigid members to the struts for limited pivotal movement about an axis transverse to the struts of the wearer at a location below the knee; and
means mounting the first and second members for relative pivotal movement between a first generally aligned position corresponding to a straight leg position of the wearer wherein the first and second arcuate guard portions are substantially nested over the knee and a second position wherein the members are inclined to each other corresponding to a bent leg position of the wearer wherein the first and second arcuate guard portions are substantially unnested; and
means mounting the first rigid member to the struts for limited pivotal movement about an axis transverse to the struts at a location above the means mounting the first and second members for pivotal movement.

10. The protective guard of claim 9 wherein the first member includes a slot and the means mounting the first rigid member to the strut comprises a pin carried by the strut and extending into the slot.

11. A protective knee guard comprising
a first rigid member providing a first arcuate guard portion for overlying a knee of a wearer;
a second rigid member providing a second arcuate guard portion for overlying the same knee of the wearer;
means for releasably attaching the first member to the leg of the wearer at a location above the knee comprising a pair of generally parallel struts and a thigh band attached to the struts for encircling the leg of the wearer above the knee and means rigidly mounting the first rigid member to the struts;
means for releasably attaching the second member to the leg of the wearer at a location below the knee; and
means mounting the first and second members for relative pivotal movement between a first generally aligned position corresponding to a straight leg position of the wearer wherein the first and second arcuate guard portions are substantially nested over the knee and a second position wherein the members are inclined to each other corresponding to a bent leg position of the wearer wherein the first and second arcuate guard portions are substantially unnested.

12. A protective knee guard comprising
a first rigid member providing a first arcuate guard portion for overlying a knee of a wearer comprising a hemicylindrical upper section for receiving the thigh of the wearer and a partially spherically shaped lower section;
a second rigid member providing a second arcuate guard portion for overlying the same knee of the wearer;
means for releasably attaching the first member to the leg of the wearer at a location above the knee;
means for releasably attaching the second member to the leg of the wearer at a location below the knee; and
means mounting the first and second members for relative pivotal movement between a first generally aligned position corresponding to a straight leg position of the wearer wherein the first and second arcuate guard portions are substantially nested over the knee and a second position wherein the members are inclined to each other corresponding to a bent leg position of the wearer wherein the first and second arcuate guard portions are substantially unnested.

13. The protective guard of claim 12 wherein the second rigid member comprises a hemicylindrical lower section for receiving the shin of the wearer and a partial spherically shaped upper section, the spherically shaped sections being nested one under the other.

14. The protective knee guard of claim 13 wherein the spherically shaped section of the second rigid member resides under the spherically shaped section of the first member.

* * * * *